United States Patent [19]

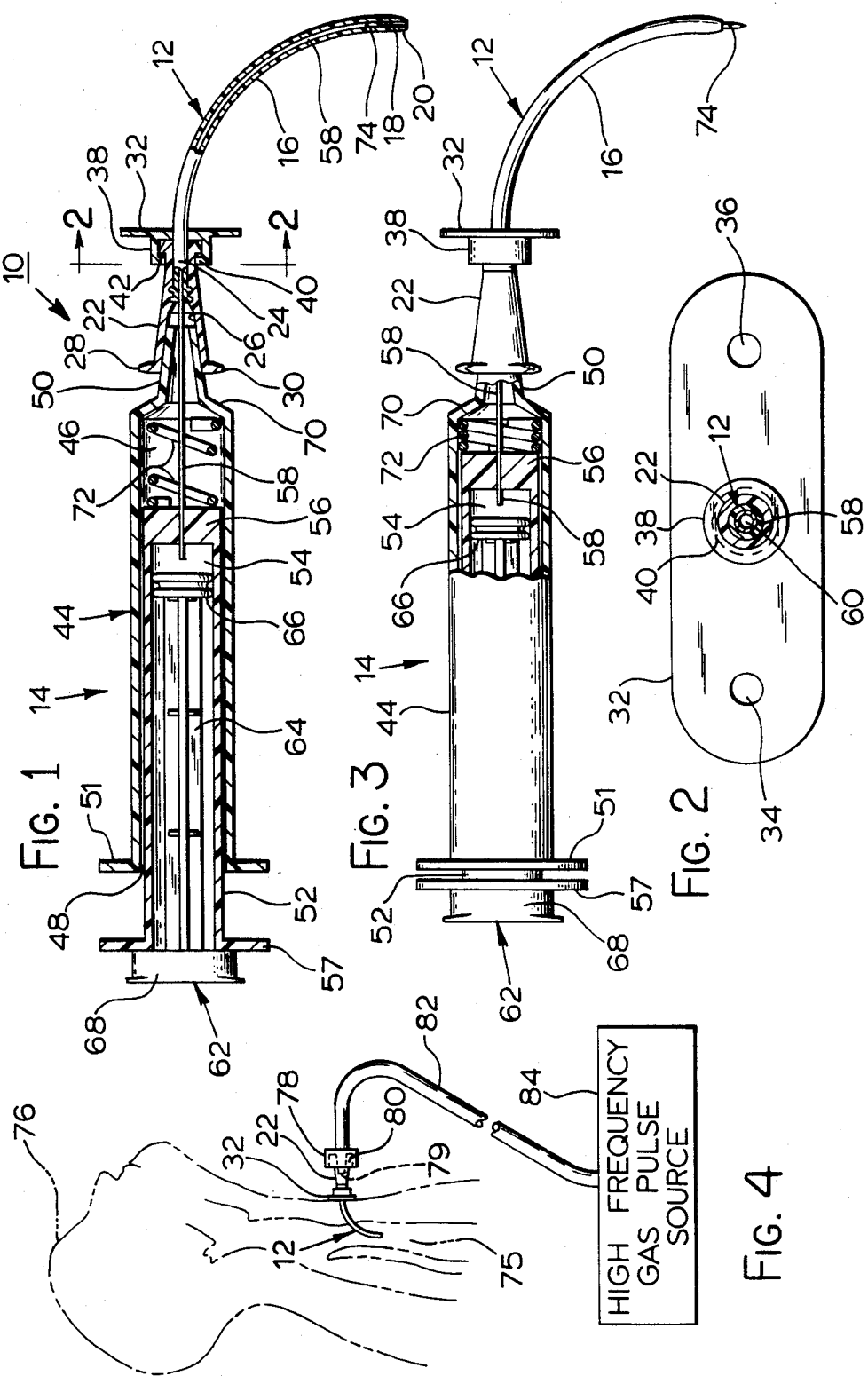

Shen

[11] Patent Number: 4,488,545

[45] Date of Patent: Dec. 18, 1984

[54] CATHETER PLACEMENT DEVICE

[75] Inventor: S. Nancy Shen, St. Louis, Mo.

[73] Assignee: Sherwood Medical Company, St. Louis, Mo.

[21] Appl. No.: 448,449

[22] Filed: Dec. 10, 1982

[51] Int. Cl.³ .............................................. A61M 16/00
[52] U.S. Cl. ........................... 128/200.26; 128/207.14;
604/900; 604/227; 604/165; 604/168
[58] Field of Search ...................... 128/200.26, 207.14,
128/207.15, 305.3; 604/22, 168, 900, 227, 243,
240, 164, 165, 166

[56] References Cited

U.S. PATENT DOCUMENTS

| | | | |
|---|---|---|---|
| 2,389,355 | 11/1945 | Goland et al. | 604/165 |
| 3,030,959 | 4/1962 | Grunert | 128/329 |
| 3,046,985 | 7/1962 | Saenz | 604/227 |
| 3,094,122 | 6/1963 | Gauthier et al. | |
| 3,682,166 | 8/1972 | Jacobs | 128/207.14 |
| 3,714,945 | 2/1973 | Stanley | 604/164 |
| 3,727,613 | 4/1973 | Sorenson et al. | 604/165 |
| 4,292,970 | 10/1981 | Hession, Jr. | 604/164 |

FOREIGN PATENT DOCUMENTS 378629 7/1923 Fed. Rep. of Germany ...... 604/165

OTHER PUBLICATIONS

Klain, "High Frequency Ventilation in Respiratory Care", May 1981, vol. 26, No. 5, pp. 427-429.
Klain et al., "High Frequency Jet Ventilation in CPR", Critical Care Medicine, May 1981, pp. 421-422.
Boysen, "High Frequency Ventilation", Respiratory Therapy, Sep./Oct. 1982 pp. 105-106.

Primary Examiner—Henry J. Recla
Attorney, Agent, or Firm—Stanley N. Garber; Gregory E. Upchurch; William R. O'Meara

[57] ABSTRACT

A catheter placement device for use in introducing high frequency jet ventilation gas to the trachea of a patient is provided which includes a catheter, and a catheter introducer having a needle within the catheter and includes an actuating member for moving the needle to an extended position in which the needle tip extends beyond the distal end of the catheter for percutaneously inserting the catheter and needle into the throat of a patient. A spring moves the needle tip to a retracted position within the catheter upon release of the actuating member. The introducer is removable from the catheter so that a source of high frequency ventilation gas can be connected to the catheter. The introducer has a piston which is movable in a bore which communicates with the needle lumen.

19 Claims, 4 Drawing Figures

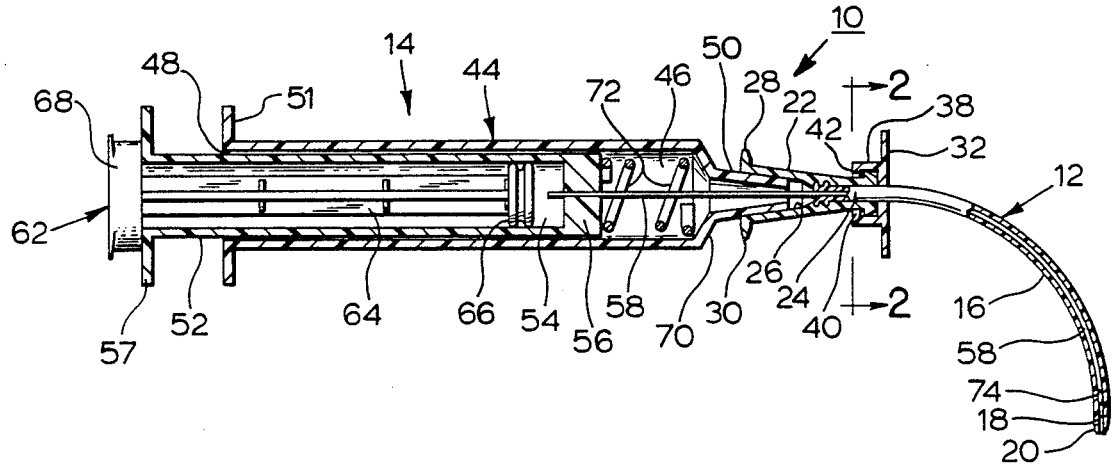

CATHETER PLACEMENT DEVICE

DESCRIPTION

1. Technical Field

This invention relates to catheter placement devices and, more particularly, to a catheter placement device for high frequency jet ventilation.

2. Background Art

In conventional respiratory ventilation systems, physiological volumes of gas are delivered to the airway and lungs of the patient, for example, by means of an endotracheal or tracheostomy tube. Gas is cyclically introduced into the lungs of the patient at the normal breathing frequency, for example, twenty times a minute, to perform the breathing function or to assist the patient in breathing.

In recent years, use of high frequency ventilation, referred to herein as "HFV", has been under consideration and has been used to a limited degree. In HFV systems, such as in high frequency jet ventilation, referred to herein as "HFJV", pulses of gas at a frequency substantially higher than the normal respiratory or breathing frequency and at a higher velocity are applied to the patient's airway. In HFJV, pulses of gas, for example, at a frequency between 100 and 500 cycles per minute, are introduced into the airway through a tube or cannula inserted into the trachea. The cannula is substantially smaller in diameter than the conventional tracheal tubes required by conventional ventilation systems. The pulses of gas flowing toward the lungs facilitate gas diffusion and enhance gas exchange by the lungs. Because of the low tidal volume required in HFJV, the risk of pulmonary barotrauma is reduced. HFJV is also believed to minimize circulatory depression while maintaining adequate gas exchange. It may also be useful for a patient who is breathing spontaneously and has difficulty in breathing in step with a conventional ventilator. The need for muscular relaxants and/or sedatives often used in conventional ventilation systems is reduced or eliminated because HFJV can be superimposed on spontaneous breathing.

HFJV can be administered by percutaneously inserting a cannula into the trachea of the natural airway by means of a cricothyroid puncture. The cannula is properly positioned in the trachea and connected to a source of high frequency gas. The cannulas used are of relatively small sizes, such as flexible 12, 14 and 16 gauge cannulas having inner diameters of between about 1 mm and 2 mm. In comparison, the typical tracheostomy tube for adult use may have an inside diameter of 6 mm or more.

Because a small cannula is used, it can be inserted quickly and easily, and with local anesthetic. The cannula can be introduced into the trachea with little trauma to the throat, for example, by using a needle extending through the cannula with its pointed end beyond the distal end of the cannula during insertion. Because of the relatively small size of cannula used in HFJV compared to the size of a tracheal tube used in conventional ventilation systems, there is less trauma, and in general, greater patient acceptance.

The HFJV cannula has been percutaneously introduced into the trachea by placing the cannula on a hypodermic needle of a syringe and inserting the needle and cannula through the cricothyroid membrane into the trachea of the patient. When the cannula and needle are believed to be within the trachea, the piston of the syringe may be withdrawn or moved proximally in the syringe barrel to determine if the trachea has been entered. If air is aspirated, the insertion into the trachea is known to be successful. The needle and cannula may be curved for ease of insertion, since the needle and cannula enter the trachea at an angle to the longitudinal axis of the trachea. After entering the trachea, the cannula is moved until it is properly disposed in the trachea, and this may be done using the needle as a stylet to avoid any kinking of the cannula. The syringe and needle are then removed from the cannula while the cannula remains in the trachea. A source of high frequency gas is connected to the exterior or proximal end of the cannula to effect jet ventilation of the patient.

Some problems associated with the above procedure are that, where both needle and catheter are manipulated to move them into the trachea after entering the airway, the needle has to be moved proximally relative to the catheter such that the tip of the needle is retracted to a position within the distal end of the cannula so as to avoid or reduce the chance of inadvertently stabbing the patient. On the other hand, if the needle is moved too far into the cannula, a kink in the cannula might occur when moved in the airway, depending upon the cannula material and handling of the cannula. While different persons will manipulate the cannula and needle in different manners in an attempt to accomplish a satisfactory catheter insertion, it has been a tedious insertion procedure and with some danger of inadvertently damaging the patient.

SUMMARY OF THE INVENTION

It is an object of the present invention to provide an improved catheter placement device usable for high frequency jet ventilation which is relatively safe, simple and easy to use, and wherein one or more of the above-mentioned problems or disadvantages of past devices are overcome.

In accordance with one aspect of the present invention, a catheter placement device is provided which includes a catheter, a needle slideable in the catheter and having a pointed tip, means for manually moving the needle into an extended position with the pointed tip beyond the distal end of the catheter, whereby the needle and catheter can be inserted through body tissue into the desired body location, and resilient means for moving the needle from the extended position to a retracted position in which the pointed tip is within the catheter.

These, as well as other objects and advantages of the present invention, will become apparent from the following description and accompanying drawing.

BRIEF DESCRIPTION OF THE DRAWING

FIG. 1 is a cross-sectional side view of a catheter placement device for high frequency jet ventilation systems in accordance with a preferred embodiment of the invention;

FIG. 2 is an enlarged cross-sectional view taken along line 2—2 of FIG. 1.

FIG. 3 is a side view, partly in section, of the device of FIG. 1, but with the device actuated for performing a percutaneous insertion into the airway of a patient; and FIG. 4 illustrates an HFJV system in which the catheter of the device of FIG. 1 is on a reduced scale and shown inserted into the trachea of a patient and connected to a source of ventilation gas.

DETAILED DESCRIPTION OF THE PREFERRED EMBODIMENT

Referring now to the drawing, and particularly to FIG. 1, there is shown for illustration a catheter placement device 10 for use in supplying high frequency jet ventilation to a patient. The catheter placement device 10 includes a ventilation catheter 12, and a catheter introducer indicated generally at 14 for effecting percutaneous insertion of the catheter into the trachea of a patient.

The ventilation catheter 12 includes a catheter, tube or cannula 16 having a lumen 18. The cannula 16 is preferably made of a material which is resistive to kinking, flexible and substantially inert to blood, for example, it may be formed of a suitable plastic such as Teflon (polytetrafluoroethylene). The cannula 16 is curved or generally arcuate over the major portion of its length in its normal or unrestrained condition and it is open at the distal end which is indicated at 20. Cannula 16 is made so that lumen 18 has a relatively small diameter in order to obtain a pulse or flow of gas of relatively high velocity. The size of the cannula lumen chosen for any given case may vary, and will depend upon such variables as the size of the patient, pressure of the gas source, etc. The cannula 16 may be, for example, a 12, 14 or 16 gauge cannula previously mentioned herein.

Catheter 12 has a connector 22, shown as a female luer lock connector or adapter that is connected to the cannula 16 at its proximal end portion, indicated at 24. The connector 22 may be made of a suitable plastic, such as polypropylene, and that is molded about the distal end portion 24 of the cannula 16 to fix the connector and cannula together. Luer connector 22 has a conventional luer tapered bore 26 and a pair of diametrically opposite, conventional luer lock threads or ears 28 and 30 at the proximal end of the connector.

Catheter 12 also has a neck fastening strap or flange 32 connected to the cannula 16 adjacent the proximal end 24, and distally of connector 22. Flange 32, as seen in FIG. 2, is provided with a pair of holes 34 and 36, which may be employed to suture the flange to the external side of the neck of the patient to maintain the catheter 12 in place after insertion and removal of the introducer 14. Instead of suturing flange 32, other fastening means, such as tape, may be used where desired. The flange 32 is shown having a hub 38 with an open proximal end for receiving the distal end of connector 22. Hub 38 has an annular, radially inwardly extending integral lip 40 which snaps into an annular groove 42 on connector 22 when the flange 32 is placed on the connector to connect the flange and connector together. The flange may be made of a suitable plastic, for example, a relatively soft silicone rubber for patient comfort.

The catheter introducer 14 includes a housing 44 shown as a cylindrical member or barrel which is circular in cross-section and has a bore or chamber 46 open at both ends, and which extends entirely through the housing. Housing 44 is provided with an integral, male luer tip connector 50 at the distal end of the housing. The luer tapered housing tip 50 is shown inserted into the luer tapered bore 26 of the catheter connector 22 to releasably connect the catheter 12 with the introducer 14. The housing has an integral, radial outwardly extending flange 51 at the proximal end for use when employing the placement device 10, as will be discussed hereafter.

Disposed in the bore 46 is a slideable needle actuating member 52 shown in the form of an elongate hollow rod or plunger having a chamber or cylindrical bore 54 open at the proximal end. Actuating member 52 has an end member or end wall 56 closing the distal end of bore 54, and a flange 57 at the proximal end, the end wall and flange being shown as integral parts of member 52. Fixed to actuating member 52 is a catheter introducer needle 58 extending into cannula 16 of the catheter. The distal end portion of needle 58 extends through the catheter connector 22 and the tip 50 of housing 44, and is fixedly connected to the end wall 56 for concerted movement with the actuating member 52. End wall 56 may be of plastic and be molded about the proximal end of needle 58, or connected in some other manner, for example, the needle may be pressed through an opening provided in the center of the end wall to effect a tight friction fit with the actuating member 52.

For purposes to be described hereafter, the needle 58 is preferably a hollow needle having a lumen 60 as seen in FIG. 2. The needle 58 is shown generally arcuately curved over the major portion of its length and complementary in shape to the cannula 16. Needle 58 is shown extending through end wall 56 so that the needle lumen 60 is in fluid communication with the bore 54 of actuating member 52. Slideably received in bore 54 is a plunger 62 having a piston rod 64 carrying a piston 66, for example, of rubber. The piston 66 slideably and sealingly engages the sidewalls of bore 54. Piston rod 64 extends proximally outwardly of actuating member bore 54 and is provided with a finger grasping member or head 68 which is proximal of and engageable with the proximal end flange 57 of actuating member 52. The needle lumen 60 communicates with bore 54 on the distal side of piston 66.

Disposed in bore 46 between end wall 56 of needle actuating member 52 and the radially inwardly extending end wall, indicated at 70, of the housing 44, is a resiliently compressible member shown as a spring 72. Spring 72 opposes movement of the actuating member 52 and needle 58 in a distal direction from the position of these elements in FIG. 1. In FIG. 1, the actuating member 52 and needle 58 are in a predetermined retracted position with the tip of the needle, indicated at 74, retracted or withdrawn into the lumen 18 of the catheter, that is, with the needle tip 74 fully proximally of the cannula distal end 20 but close to the distal end 20. For example, in the retracted position the distal tip of the needle 58 may be 2 mm or 3 mm from the distal tip of the cannula 18. Spring 72 is shown as a metal coil spring surrounding a proximal portion of needle 58 in housing chamber 46. Needle 58 is preferably made of a metal such as stainless steel and the tip is pointed and sharp for easy insertion into body tissue. The housing 44 and actuating member 52 are preferably formed of a suitable transparent plastic such as polypropylene or the like. The piston head and rod of plunger 62 may also be of a plastic such as polypropylene.

By moving the needle actuating member 52 distally relative to housing 44, the catheter placement device is actuated to place the needle in a predetermined needle actuated or extended position shown in FIG. 3. In this position, the needle and cannula can be percutaneously inserted into the patient's airway. The needle 58 can be readily moved to the extended position with one hand, for example, by placing the index and next adjacent fingers under housing flange 51 and pressing plunger head 68 with the thumb. This causes head 68 to move the actuating member 52 distally against the force of spring 72, thereby compressing the spring and moving needle 58 distally within lumen 18 of cannula 16. The parts are shown dimensioned such that when the spring 72 is fully compressed as in FIG. 3, the needle extends beyond the distal end of cannula lumen 18 a desired or predetermined distance, the spring preventing further distal movement of the needle. If desired, the parts of device 10 could be dimensioned to allow the flanges 51 and 57 to engage and simultaneously position the needle tip 74 in a desired extended position without fully compressing spring 72.

Upon removal of the force applied to the actuating member 52 to maintain the needle extended as in FIG. 3, the needle 58 and actuating member 52 are immediately automatically retracted to the predetermined positions shown in FIG. 1 due to the forces of spring 72. Thus, spring 72 biases or returns the needle 58 to its retracted position so that the tip 74 is again fully within the cannula 16 but adjacent the end 20.

If the plunger head 68 is grasped and moved leftwardly or proximally relative to actuating member 52, piston 66 moves proximally in the bore 54 reducing the pressure or effecting a negative pressure in the bore on the distal side of piston 66 and in the lumen 60 of needle 58. Plunger 64 and bore 54 can be used in this manner as a syringe and provide an indication of the position of the needle tip 74 during insertion of the needle 58 and cannula 16. If the needle tip enters the airway of the patient, such proximal movement of plunger 62 effects aspiration of air into the chamber 54 and allows the plunger to move proximally with little resistance. Should the proximal movement of plunger 62 result in the aspiration of blood into chamber 54, or if it can be moved only a limited amount and with resistance, it is apparent that the distal tip 74 of needle 58 and distal end 20 of cannula 16 are not within the trachea of the patient.

The catheter placement device 10 may be packaged in the condition shown in FIG. 1, that is, with the spring in its expanded condition and the needle 58 in its retracted position. The device is preferably packaged in a sterile condition so that it can be used immediately upon the opening of the package.

When using device 10, the needle 58 is moved to its extended actuated position as in FIG. 3, and the extended pointed needle tip 74 and end 20 of cannula 16 are moved into the throat through the cricothyroid membrane and into the patient's airway. During this percutaneous insertion, if desired, movement of the device 10 may be halted and the piston head 68 moved proximally to move piston 66 proximally in bore 54 to provide an indication of the internal position of the needle tip 74, as previously mentioned. After the needle 58 and cannula 16 have entered the airway, the thumb pressure on head 68 is released so that the spring 72 automatically moves actuating member 52 and the needle 58 to the predetermined retracted position with the needle tip 74 proximally of end 20 of the cannula 16 (FIG. 1). With the needle 58 in the retracted position in cannula 16, both needle and cannula may be further moved while in the trachea without danger of the needle inadvertently piercing or damaging the walls of the patient's airway. The needle serves as a stylet for cannula 16 so that it can be moved without kinking or closing. The cannula 16 and needle 58 are preferably moved downwardly in the trachea of the airway until the flange 32 engages the exterior side of the neck. The introducer 14 may then be removed from the inserted catheter 12 by grasping the housing 44 and simultaneously rotating and pulling it from the luer tapered bore 26 of connector 22. With the introducer 14, including needle 58, removed from the catheter 12, the introducer may be deposited in a waste container. The catheter cannula 16, if it is not already in the desired position, may be further adjusted. The flange 32 may be sutured to the skin using holes 34 and 36, or the flange may be otherwise connected and secured to the neck of the patient to secure the catheter 12 in place.

In FIG. 4, an HFJV system is illustrated in which the catheter 12 is shown extending into the neck and into the trachea, indicated at 75, of a patient shown in phantom at 76. A conventional male luer lock connector 78 is shown sealingly connected to the catheter connector 22. As is well known, a male luer lock connector, such as connector 78, has a conventional luer tapered member 79, similar to housing tip 50, which is received in bore 26 of connector 22 in fluid-tight relation, and a surrounding hub 80 with threads (not shown) for threadedly receiving the connector ears 28 and 30 (FIG. 1) to securely lock the complementary connectors 22 and 78 together. Connector 78 is connected to a ventilation gas supply tube 82 that is connected to a source 84 of high frequency ventilation gas for supplying high frequency pulses of ventilation gas through tube 82 and catheter cannula 16 to the trachea 74 and lungs of the patient 76. The small distal end opening of the cannula 58 serves as a jet to effect relatively high velocity pulses of gas. Such pulses effect air entrainment in the trachea enhancing tidal volume. The frequency of the HFJV system is generally substantially greater than the normal breathing rate or frequency and may be several hundred cycles per minute, for example, 200 cycles per minute may be used.

The return spring 72 ensures that the pointed needle tip 74 is automatically, quickly and fully retracted into the cannula 16 upon removal or release of the manually applied force on actuating member 52 that was applied during insertion so that the needle 58 and cannula 16 can be safely simultaneously moved relative to the patient, for example, further into the trachea without the danger of inadvertently piercing body tissue. By retracting the needle tip in this manner, the insertion procedure is generally accomplished more quickly and with greater assurance of safety to the patient. Since the needle tip is retracted but still adjacent the distal end of the cannula 16, the needle also serves as a stylet to prevent collapse or kinking of the flexible cannula 16 as it is moved in the patient's airway.

Since the cylindrical housing 44 of the catheter introducer 14 has a luer tapered tip 50, it is easily and quickly selectively connected and disconnected from the female luer lock connector 22. Also, the same connector 22 is conveniently used as a tube connector to connect the catheter to gas supply tube 82.

As various changes could be made in the above construction without departing from the scope of the invention, it is intended that all matter contained in the above description or shown in the accompanying drawing shall be interpreted as illustrative and not in a limiting sense.

I claim:

1. A catheter placement device comprising a cannula having a proximal end and a distal end, a cannula introducer needle having a proximal end and a distal end slideable in and removable from said cannula and having a lumen therethrough and a pointed tip at the distal end thereof, and means for manually moving said needle distally into an extended position in said cannula in which said tip is disposed distally of the distal end of said cannula for passing the distal ends of said needle and said cannula through body tissue and into a desired body location and for moving said needle proximally from the extended position to a retracted position in which said tip is disposed within said cannula, said means for manually moving said needle including an elongated housing having a chamber therein with an open proximal end and wall means at the distal end thereof for connection with the proximal end of said cannula, an actuating member slidably mounted in the chamber of said housing and extending proximally therefrom, said actuating member having a bore extending therethrough with an open proximal end and wall means at the distal end thereof for connecting and fluidically communicating the bore thereof with the lumen of said needle, said wall means of said actuating member being affixed to the proximal end of said needle for moving said needle relative to said cannula, piston means slidably mounted in the bore of said actuating member for effecting a negative pressure in said lumen, said piston means having a proximal end extending proximally from said actuating member, whereby said housing, actuating member and piston means are arranged telescopically one within the other and further include, at each proximal end thereof, gripping means adapted to be engaged by the fingers, and resilient means for biasing said actuating member and therefore, said needle from the extended position to the retracted position.

2. The device of claim 1 wherein said needle and said cannula are normally generally arcuate over the major portions of their lengths.

3. The device of claim 1 wherein said cannula includes a luer tapered connector connected to the proximal end of said cannula for receiving a complementary luer tapered connector in fluid communication with said cannula.

4. The device of claim 3 wherein said cannula is flexible and of plastic material, and said housing is releasably connectable to said cannula.

5. The device of claim 1 including complementary means includes first and second luer tapered connectors respectively on said housing and said cannula, said cannula and needle being sized to enter the neck and trachea of a patient.

6. The device of claim 1 wherein said resilient means is disposed in said housing between the distal ends of said actuating member and housing, said pistion means including a rod extending proximally from the proximal end of said housing for manually moving said piston means.

7. A high frequency jet ventilation catheter placement device for use in supplying ventilation gas to the airway of a patient, comprising a flexible ventilation cannula having a proximal end and a distal end and including first connector means connected to the proximal end of said cannula and adapted for connection with a ventilation gas supply tube, an elongated housing having a chamber therein with an open proximal end and second connector means at the distal end thereof detachably connected to said first connector means, a needle having a length greater than that of said cannula and having a lumen therethrough terminating in a tissue piercing point at the distal end thereof, said needle slidably positioned in said cannula and having a proximal end extending into the chamber of said housing a manually movable actuating member slidably mounted in the chamber of said housing and extending proximally therefrom, said actuating member having a bore extending therethrough with an open proximal end and wall means at the distal end thereof for connecting and fluidically communicating the bore thereof with the lumen of said needle, said wall means of said actuating member being affixed to the proximal end of said needle for moving said needle relative to said cannula, spring means associated with said housing for resisting movement of said actuating member and said needle in a distal direction from a retracted needle position in which said needle point is within said cannula to an extended position in which said needle point is distally of the distal end of said cannula, said actuating member being manually movable in response to a manually applied force thereto to move said needle to the extended position so that said needle and cannula can be moved in concert to penetrate body tissue of a patient and position the distal end of said cannula and said needle point in the airway of a patient, and plunger means slidably positioned in the bore of said actuating member and having a proximal end extending proximally from said actuating member and a piston at the distal end thereof in said bore within said actuating member in sealing sliding engagement with the walls of said bore for effecting a negative pressure in said bore of said actuating member and in said lumen in response to movement of said plunger proximally relative to said bore, said housing, actuating member and plunger means being arranged telescopically one within the other and further include, at each proximal end thereof, gripping means adapted to be engaged by the fingers whereby said needle is automatically movable proximally from the extended position to the retracted position by the force of said spring means in response to the removal of the manually applied force on said actuating member and said needle is removable proximally out of said cannula upon detachment and movement of said housing proximally from said first connector means.

8. The device of claim 7 wherein said cannula includes flange means connected to said the proximal end thereof adjacent said first connector means for securing said catheter to the neck of a patient.

9. The device of claim 7 wherein said second connector means includes a luer slip tip insertable into said first connector means.

10. The device of claim 7 wherein a major portion of said needle and said cannula are generally complementary arcuately shaped in their unrestrained conditions.

11. The device of claim 7 wherein said housing and said actuating member are generally circular in cross-section and have a common longitudinal axis.

12. The device of claim 8 wherein said cannula further includes flange means for connecting said cannula to the neck of a patient, said first connector means having a proximal end to which said second connector means is attached and a distal end connected to the proximal end of said cannula, said flange means being connected to the distal end portion of said first connector means with said cannula extending through said flange means.

13. The device of claim 12 wherein said cannula and said needle are generally arcuate in shape in their normal unrestrained conditions.

14. The device of claim 7 wherein said first and second connector means include complementary luer tapered connectors respectively.

15. The device of claim 7 wherein said spring means returns said needle to the retracted position wherein said needle point is a proximally predetermined distance from the distal end of said cannula but closely adjacent thereto.

16. The device of claim 7 wherein said spring means is a metal coil spring in said housing.

17. The device of claim 7 wherein said housing, said actuating member, and said plunger are concentrically disposed substantially about a common axis.

18. The device of claim 7 wherein said gripping means on said housing, actuating member and plunger means comprise radial flanges adjacent the respective proximal ends thereof.

19. The device of claim 8 wherein said spring means is disposed in said housing between the distal ends of said actuating member and housing, said plunger means including a rod extending proximally from the proximal end of said housing for manually moving said piston.

* * * * *